US012251225B2

(12) United States Patent
Birkill et al.

(10) Patent No.: US 12,251,225 B2
(45) Date of Patent: Mar. 18, 2025

(54) NON-INVASIVE DIAGNOSTIC ASSEMBLY AND METHOD OF USING SAME

(71) Applicant: Xavant Technologies (Pty) Ltd., Pretoria (ZA)

(72) Inventors: Corlius Fourie Birkill, Rietondale (ZA); Roche Janse Van Rensburg, Pretoria (ZA); Barend Jacques Swart, Bryanston (ZA); Dawid Gideon Le Roux Van Niekerk, Pretoria (ZA); Florian Martin Lipp, Guenzburg (DE); Johan Amey Sieling, Noord-Brabant (NL)

(73) Assignee: Xavant Technologies (Pty) Ltd., Pretoria (ZA)

( * ) Notice: Subject to any disclaimer, the term of this patent is extended or adjusted under 35 U.S.C. 154(b) by 0 days.

(21) Appl. No.: 17/068,246

(22) Filed: Oct. 12, 2020

(65) Prior Publication Data

US 2021/0106270 A1     Apr. 15, 2021

Related U.S. Application Data

(60) Provisional application No. 62/914,376, filed on Oct. 11, 2019.

(51) Int. Cl.
*A61B 5/00* (2006.01)
*A61B 5/257* (2021.01)
(Continued)

(52) U.S. Cl.
CPC .............. *A61B 5/296* (2021.01); *A61B 5/257* (2021.01); *A61B 5/273* (2021.01)

(58) Field of Classification Search
CPC ......... A61B 5/1106; A61B 5/296; A61B 5/24; A61B 5/389; A61B 5/6826; A61B 5/6833; A61B 5/7217; A61B 5/685; A61B 5/257
(Continued)

(56) References Cited

U.S. PATENT DOCUMENTS

2006/0253167 A1*  11/2006  Kurtz ....................... A61B 5/24
                                                          607/48
2007/0185409 A1    8/2007  Wu et al.
(Continued)

FOREIGN PATENT DOCUMENTS

WO    2013172830 A1    11/2013
WO    2016196801 A1    12/2016
(Continued)

OTHER PUBLICATIONS

International Search Report and Written Opinion dated Apr. 1, 2021 from PCT International Appln. PCT/IB2020/000842.
(Continued)

*Primary Examiner* — Joseph A Stoklosa
*Assistant Examiner* — Brian M Antiskay
(74) *Attorney, Agent, or Firm* — Amster, Rothstein & Ebenstein LLP

(57) ABSTRACT

A non-invasive diagnostic assembly that includes an interface configured for connection to a diagnostic monitoring device; a plurality of electrodes configured for adhesion to a patient's skin at respective locations and electrically connected to the interface; and at least one adjustable connection segment having a concertina/accordion/ripple-shaped configuration connecting at least two electrodes of the plurality of electrodes.

19 Claims, 12 Drawing Sheets

(51) Int. Cl.
*A61B 5/273* (2021.01)
*A61B 5/296* (2021.01)

(58) Field of Classification Search
USPC ......... 600/372, 382–393; 607/108, 111–112, 607/115, 118
See application file for complete search history.

(56) References Cited

U.S. PATENT DOCUMENTS

| | | |
|---|---|---|
| 2014/0012157 A1 | 1/2014 | Gilhuly |
| 2014/0235991 A1 | 8/2014 | Gadsby |
| 2015/0088224 A1 | 3/2015 | Goldwasser et al. |
| 2015/0174391 A1 | 6/2015 | Wistrand et al. |
| 2018/0036535 A1 | 2/2018 | Wong et al. |
| 2018/0307314 A1 | 10/2018 | Connor |
| 2019/0008453 A1 | 1/2019 | Spoof |
| 2019/0223764 A1* | 7/2019 | Hulvershorn ........ A61B 5/1106 |

FOREIGN PATENT DOCUMENTS

| | | |
|---|---|---|
| WO | 2019124274 A1 | 6/2019 |
| WO | 2019126340 A1 | 6/2019 |

OTHER PUBLICATIONS

Supplemental EP Search Report dated Oct. 23, 2023 issued in European Patent Application No. EP 20873607.

* cited by examiner

NON-INVASIVE DIAGNOSTIC ASSEMBLY AND METHOD OF USING SAME

CROSS-REFERENCE TO RELATED APPLICATIONS

The present application claims benefit of and priority to U.S. Provisional Patent Application Ser. No. 62/914,376 filed Oct. 11, 2019 entitled NON-INVASIVE DIAGNOSTIC ASSEMBLY AND METHOD OF USING SAME, the entire content of which is hereby incorporated by reference herein.

BACKGROUND

Filed of the Disclosure

The present disclosure is generally related to a non-invasive diagnostic assembly for use with an electronic monitoring device.

RELATED ART

Advancements in non-invasive diagnostics are continuing to be developed. One example is the use of electrical signals generated and detected at various locations on a patient's skin to diagnose underlying muscular function. More particular examples include monitoring the efficiency of neuromuscular transmission (NMT) as it relates to the use of neuromuscular blocking agents. This is achieved by stimulation of nerves (motor neurons) and using electromyography (EMG) to assess the resultant muscle response. Existing EMG electrode assemblies used for NMT monitoring include the Blink™ Twitchview™ (element 400 shown in FIG. 4A, for example) and the Senzime™ Tetragraph™ (element 405 shown in FIG. 4B). These assemblies 400 and 405 are used to monitor, in this example, muscular and neural functions at a patient's hand. In particular, adhesive patches incorporating electrodes, which are connected to one another via connector segments (410 and 415 in FIGS. 4A and 4B), are applied to various locations on the skin of a patient so that a stimulation signal may be applied to one or more locations and measurement signals may be detected at one or more different locations.

One of the issues complicating application of these electrode assemblies is that the variance in hand size of a wide demographic of patients results in difficulty in stabilizing the electrodes. The above-described conventional electrode assemblies include substantially flat, connector segments (410 and 415 in FIGS. 4A and 4B) between electrode patches such that slack in these connector segments may be substantial, depending upon the size of a patient's hand—for example, as illustrated by the slacked connector segments 415 shown in FIG. 4B. Excessive slack may contribute to difficulty in maintaining a stable application of the electrodes to the patient's skin—e.g., strain on the adhesion to the skin requiring additional adhesive strength. Where a connection is not secure, the data collected by the electrode may not be reliable. The slack also increases the likelihood of the connector getting caught or pulled which would pull the electrodes away from the user's skin which would interrupt treatment. At the same time, connector segments that do not have sufficient length may not be usable for patients with larger hands.

Accordingly, it would be desirable to provide a non-invasive diagnostic assembly that avoids these and other problems.

SUMMARY

In light of the above, an improved non-invasive diagnostic assembly is disclosed.

The present disclosure is generally related to an improved non-invasive diagnostic assembly for use with an electronic monitoring device.

In accordance with an embodiment of the present disclosure, a non-invasive diagnostic assembly includes: an interface configured for connection to a monitoring device; a plurality of electrodes configured for adhesion to a patient's skin at respective locations and electrically connected to the interface; and at least one adjustable connection segment connecting at least two electrodes of the plurality of electrodes.

In embodiments, the at least one adjustable connection segment includes a conductor element providing an electrical connection between the at least two electrodes.

In embodiments, the at least one adjustable connection segment includes a plurality of segment elements connected to each other such that the at least one connection segment expands when force is applied in a first direction and contracts when force is applied in a second direction, opposite the first direction.

In embodiments, the at least one adjustable connection segment includes a conductor element providing an electrical connection between the at least two electrodes.

In embodiments, the non-invasive diagnostic assembly includes a second adjustable connection segment connecting at least one of the at least two electrodes to a third electrode.

In embodiments, the second adjustable connection segment includes a conductor element providing an electrical connection between the at least one electrode of the at least two electrodes and the third electrode.

In embodiments the second adjustable connection segment includes a second plurality of segment elements connected to each other such that the second connection segment expands when force is applied in a first direction and contracts when force is applied in a second direction, opposite the first direction.

In embodiments, the at least two electrodes of the plurality of electrodes are configured for connection to the patient's skin at respective locations along an ulnar nerve.

In embodiments, at least one electrode of the plurality of electrodes is configured for connection to the patient's skin at a location corresponding to an adductor pollicis muscle of the patient.

In embodiments, at least one electrode of the plurality of electrodes is configured for connection to the patient's skin at a location corresponding to a flexor hallucis brevis muscle of the patient.

In embodiments, at least one electrode of the plurality of electrodes is configured for connection to the patient's skin at a location corresponding to a digit on the patient's hand.

In embodiments, at least one electrode of the plurality of electrodes is configured for connection to the patient's skin at a location corresponding to a thumb of the patient.

In embodiments, at least one electrode of the plurality of electrodes is configured for connection to the patient's skin at a location corresponding to a pinky of the patient.

In embodiments, the at least two electrodes include a first electrode adhered at a location corresponding to the adductor pollicis muscle and a second electrode adhered at a location corresponding to the thumb.

In embodiments, the at least two electrodes include a first electrode adhered at a location corresponding to the adductor digiti minimi muscle and a second electrode adhered at a location corresponding to the pinky.

In embodiments, the at least two electrodes include a first electrode adhered at a location corresponding to the adductor digiti minimi muscle and a second electrode adhered at a respective location corresponding to the ulnar nerve.

In embodiments, the at least two electrodes include a first electrode adhered at a location corresponding to the adductor pollicis muscle and a second electrode adhered at a location corresponding to the ulnar nerve.

In embodiments, the interface is directly connected to a monitoring device.

In embodiments, the interface is configured for electrical connection to a monitoring device to provide data from the plurality of electrodes to the monitoring device.

In embodiments, the plurality of electrodes includes at least two stimulating electrodes and at least two detector electrodes.

BRIEF DESCRIPTION OF THE DRAWINGS

Exemplary embodiments of the present disclosure will be described with reference to the accompanying figures, wherein.

DETAILED DESCRIPTION

The present disclosure is generally related to an improved non-invasive diagnostic assembly for use with an electronic monitoring device.

Figure 1:
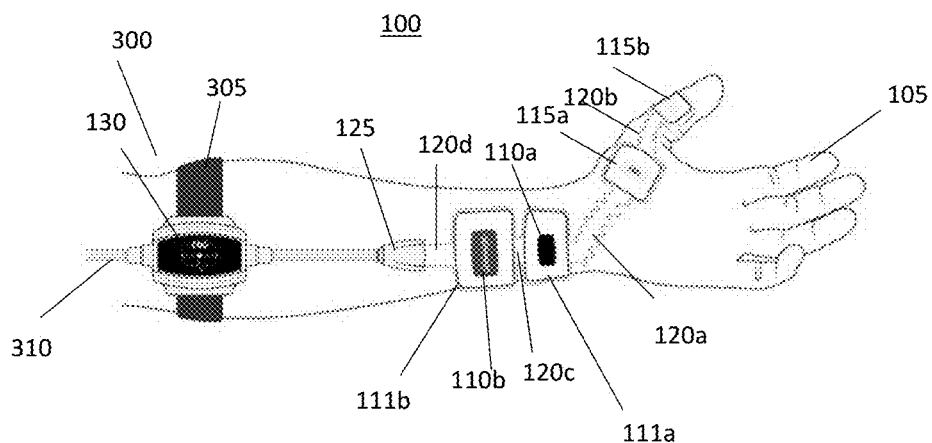
FIG. 1 illustrates an exemplary diagram of a diagnostic assembly adhered to a patient and connected to a monitoring device in accordance with an embodiment of the present disclosure.

FIG. 1 illustrates an embodiment of a diagnostic assembly 100 attached to a patient's hand 105 at a wrist and hand area of the patient for electric stimulation via one or more stimulating electrodes 110a and 110b. In embodiments, detection of muscle activity may be provided via one or more detector electrodes 115a and 115b in accordance with an exemplary embodiment of the present disclosure. In embodiments, electrodes 110a, 110b, 115a, and 115b may include flat strips/plates having metallic and/or otherwise electrically conducting materials that are disposed proximate the patient's skin and retained in place with adhesives. In embodiments, the electrodes 110a, 110b, 115a, and 115b may have a shape other than a flat strip or plate provided that they are metallic or otherwise electrically conductive. In embodiments, adhesives may be provided in or on a resilient material that partially encloses or covers the electrodes 110a, 110b, 115a and 115b to form a connected diagnostic assembly 100. In embodiments, prior to attachment to the user's hand 105, one or more backings (not shown) may be used to cover the adhesive provided on the resilient material and removed prior to attachment. In embodiments, the adhesive for applying electrodes 110a, 110b, 115a, and 115b to a patient's skin may be a liquid, a foam, a gel adhesive, and the like. In embodiments, the adhesive may be applied to the user's skin prior to application of the electrodes. In embodiments 3M 1422 adhesive may be used, however, any suitable adhesive may be used provided that it is suitable for use on human skin. In embodiment, the adhesive should not be electrically conductive.

As shown in FIG. 1, in embodiments, the stimulating electrodes 110a and 110b, may be adhered to patient's skin along the ulnar nerve, and are physically connected to detector electrode 115a via a first connection segment 120a. In embodiments, the first connection segment 120a may have an accordion shape or structure including a plurality of segments S1, S2 . . . SN movable relative to each other via a hinge-like connection to allow for expansion and contraction to adjust positioning of the stimulating electrode 110a relative to the detecting electrode 115a. In embodiments, the connection between the segments S1, S2 . . . SN may be a living hinge type connection. In embodiments, the detector electrode 115a may be physically connected to a second detector electrode 115b via a second connection segment 120b. In embodiments, the second connection segment 120b may also have an accordion shape including a plurality of segments that allow for expansion and contraction. In embodiments, adjusting the length of the first and second connection segments 120a, 120b allows for adjusting the placement of the detecting electrodes 115a, 115b relative to each other and the rest of the diagnostic assembly 100 to accommodate a wide variety of patients.

In embodiments, the first and second connection segments 120a and 120b may be made from a resilient material—e.g., a polymer, and the like. In embodiments, thermoplastic polyurethane (TPU) may be used. In embodiments, a material that allows for stretching, including in the accordion structure is suitable. In embodiments, a material that allows for silver (Ag) or another conductor to be printed on the material without breaking conductive paths is suitable and may be used. In embodiments, the connection elements 120a, 120b may include one or more conductive wires or other conducting elements or materials, such as printed or embedded conductive paths, that provide for extension and retraction to allow for placement of the detector electrodes 115a and 115b at designated locations on a patient's hand, specifically one or more digit of the user's hand (e.g., a thumb area for electrode 115b shown in FIG. 2A) or, in embodiments, on a pinky (not shown)—or a patient's palm area (not shown). In embodiments, the detector electrodes 115a or 115b may be positioned over the muscle belly of the adductor pollicis muscle such as electrode 115a shown in FIG. 2A or the flexor hallucis brevis muscle (not shown), which is in the user's foot. That is, in embodiments, the assembly 100 may be used on a patient's foot or other body parts. In embodiments, the assembly 100 may be used in conjunction with facial nerves such as the zygomatic branch of the facial nerve and corresponding orbicularis occuli muscle or the temporal nerve and the supercili muscle. The connection segments 120a and 120b may include a surface or internal channel(s) for accommodating the one or more electrical wires or other conductors electrically connecting the detector electrodes 115a and 115b to the connector 125. In embodiments, the electrical wire or other conductors may be provided in the form of a conductive path or channel provided in the segments 120a, 120b. In embodiments, a silver (Ag) or other conductive path may be printed on the connection segments 120a, 120b. In embodiments, a conductive path may be otherwise embedded in the connection segments 120a, 120b.

In embodiments, the segmented structure of the accordion structure or shape provided in the first and second connection segments 120a, 120b allows for stretching and retracting of the first and second connection segments relative to each other and to the remainder of the diagnostic assembly 100 such that the electrodes 115a, 115b may be properly placed on patients of different sizes without the need to provide differently-sized assemblies.

Figure 1A:
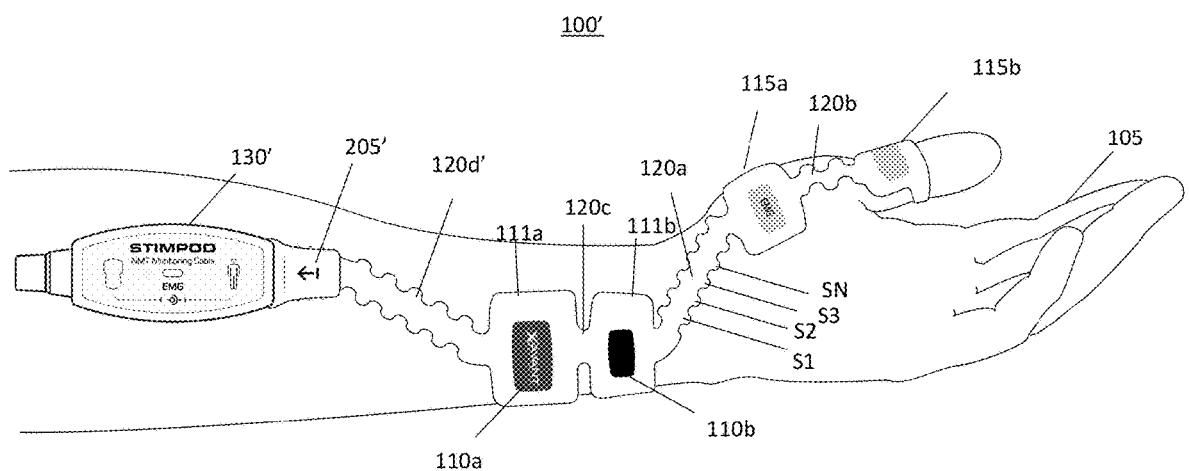
FIG. 1A illustrates an exemplary diagram of a diagnostic assembly adhered to a patient and connected to a monitoring device in accordance with another embodiment of the present disclosure.

In embodiments, as can be seen in FIG. 1A, for example, a diagnostic assembly 100' may be connected directly to the monitoring device 130' via interface 205'. In embodiments, the connection section 120d' between the stimulating electrode 110a and the interface 205' may also have an accordion structure to allow for expansion and contraction. Using the accordion structure in the connection segment 102d' allows the monitoring device 130' to be positioned anywhere around the arm. In embodiments, allowing for adjustment of the position of the monitoring device 130' is beneficial. In conventional devices, conventional connectors are often situated on the anteromedial aspect of the arm. In many situations, however, user's arms are tucked tightly against the body and these conventional connectors may lead to significant pressure on the anteromedial aspect of the user's arm which could lead to injury. Allowing for adjustment of the positioning of the monitoring device 130' allows for repositioning of the connectors, and this, may avoid this problem.

In embodiments, the monitoring device 130' may include a receiving slot 131 configured to receive metal electrode plate 206 of the interface 205' to allow for physical and electrical connection of the interface with the monitoring device. In embodiments, the diagnostic assembly 100' is otherwise substantially the same in structure and function to the diagnostic assembly 100 discussed above.

Figure 5:
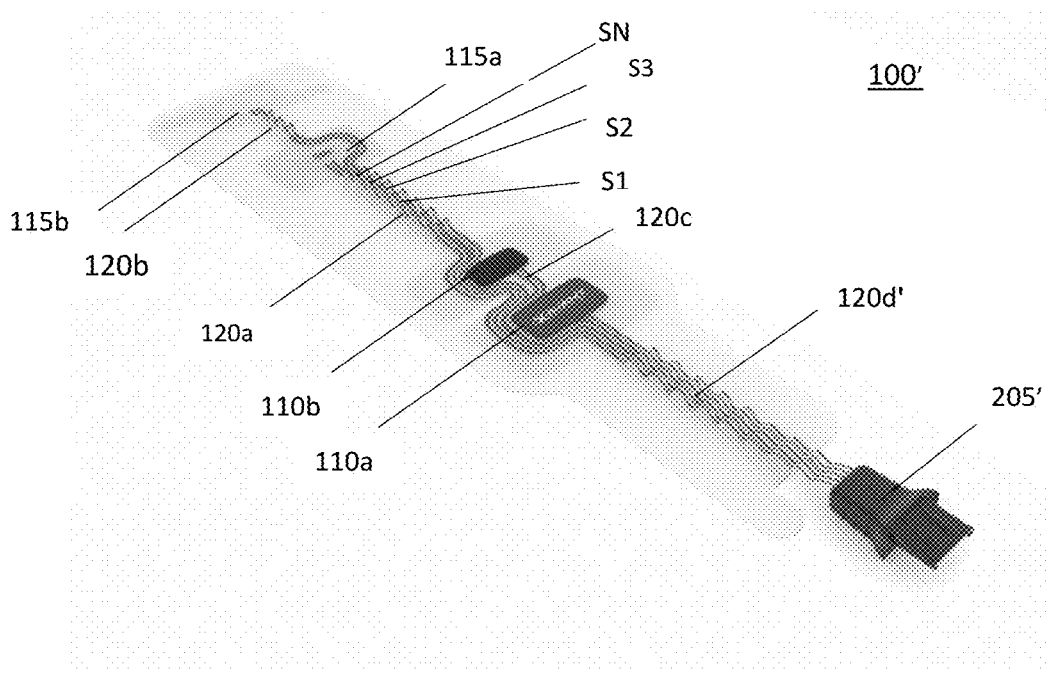
FIG. 5 illustrates the diagnostic assembly of FIG. 1A including the segments of a connection element thereof in a partially retracted, neural position.
Figure 6:
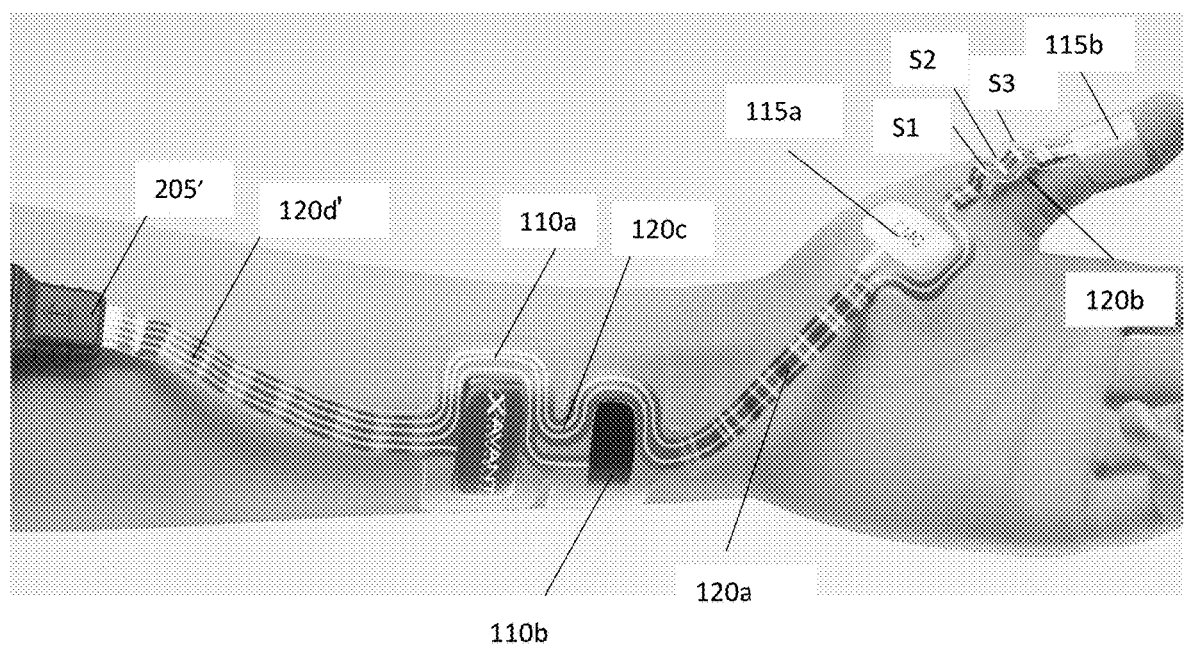
FIG. 6 illustrates the diagnostic assembly of FIG. 1A including the segments of at least one connection element in a retracted position.
Figure 7:
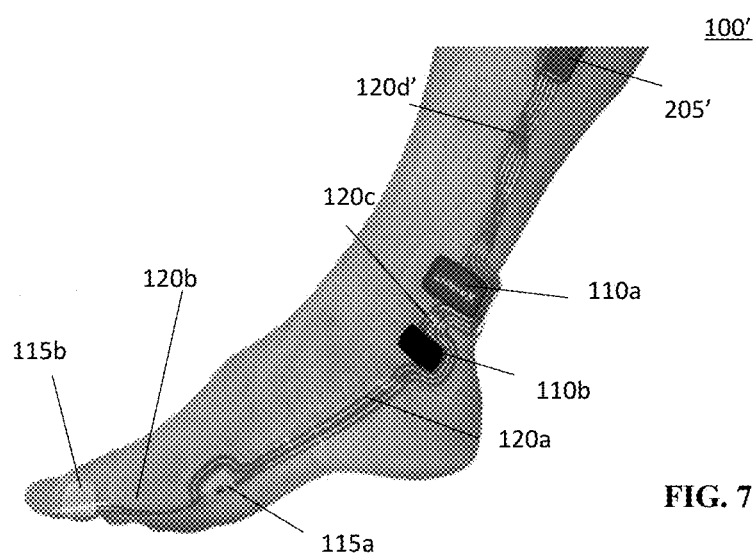
FIG. 7 illustrates the diagnostic assembly of FIG. 1A including the segments of at connection element in an extended position and used on a user's foot in accordance with an embodiment of the present disclosure.

In embodiments, the first and second connection segments 120a, 120b are made of a resilient material and are biased into a partially retracted neutral position and generally return to this partially retracted position when the electrodes 115a, 115b are not secured to the user's skin (see FIG. 5, for example). As noted above, in embodiments, the connection section 120d' may also have an accordion structure and may include the retracted neutral state discussed above. In embodiments, the segments S1, S2 . . . SN also allow for retraction of the first and second connection segments 120a and 120b (and connection segment 120d' when used) when not secured in an extended position which reduces slack in the first and second connecting segments when used on smaller patients and, thereby, reduces the strain on the adhesive used to hold the electrodes 115a and 115b to the patient's skin such that the risk of detachment or movement is minimized. Connection segment 120b in FIG. 6 illustrates an example of such a retracted position or state. Reducing slack also reduces the likelihood that the assembly 100 may be caught by or come in contact with impediments that could pull the electrodes 110a, 110b, 115a, 115b away from the user's skin. FIG. 7 shows an exemplary illustration of the connection segment 120a where the segments S1, S2 . . . SN are extended to extend the length of the connection element 120a. In FIG. 7, diagnostic assembly 100' is shown mounted on a user's foot.

As shown in FIG. 1, in embodiments, the stimulating electrodes 110a and 110b may be provided in the form of or mounted on or in patches 111a, 111b that are adhered or otherwise secured in place on the patient's skin along the ulnar nerve to provide electrical stimulus to the nerve. In embodiments, the patches 111a, 111b may be made of a resilient material and may include a layer of adhesive. In embodiments, the patches 111a, 111b made be made of a material in which adhesive is impregnated. In embodiments, adhesive may be applied to the user's skin to hold the patches 111a, 111b in desired positions on the user's body. In embodiments, the patches 111a, 111b including the stimulating electrodes 110a, 110b may be connected to or integrated with at least one of the first and second connection segments 120a, 120b. In embodiments, the detector electrode 115a measures the EMG activity of the adductor policis, which is a muscle in the hand that functions to adduct the thumb based on stimulation provided by the stimulating electrodes 110a, 110b. In embodiments, where the assembly 100 is used in treatment of a user's foot, the assembly 100 may be used to measure the EMG activity of the flexor hallucis brevis, which is in the user's foot. FIG. 7 illustrates an exemplary illustration of the assembly 100' positioned on the user's foot. In embodiments, the detector electrode 115b on the thumb may be the reference electrode for the EMG signal. As further illustrated in FIG. 1, in embodiments, electrode 110b may be connected to electrode 110a via a third connection segment 120c and the assembly 100 may be connected to interface 205 (FIG. 2A) via a fourth connection segment 120d.

Figure 8:
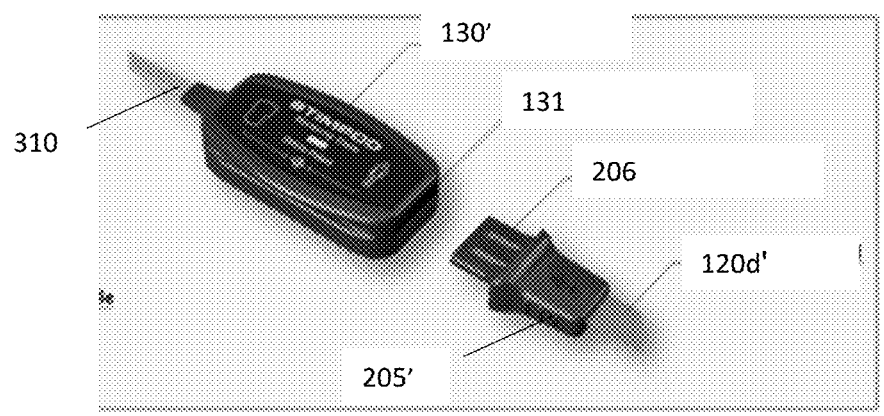
FIG. 8 illustrates a more detailed view of the monitoring device and interface of FIG. 1A.

In embodiments, various arrangements of connector wires or other conductive paths or traces may be embodied in the connection segments 120a, 120d for connecting electrodes 110a, 110b, 115a, and 115b to interface 205 (and, optionally, to one another) and, in turn, to a monitoring device 130 via connector 125 that may be configured to receive the interface 205. FIG. 8 illustrates a more detailed illustration of the monitoring device 130' which may include a slot 131 configured to receive the interface 205'. In embodiments, the slot 131 may include one or more magnets that may mate with a metal plate 206 provided in the interface 205' to hold the interface in place in the monitoring device 130' and may provide a "snap-fit" connection. In embodiments, any other suitable connector may be provided. In embodiments, the connector should be sufficient to provide for a disconnecting pull force of 0.8 kgf. In embodiments, the plate 206 may provide both a physical and electrical connection to the monitoring device 130'.

In embodiments, the monitoring device 130, 130' may be an electronic device having hardware (customer integrated circuits; individual circuit elements, or one or more processors and connected memory) and, optionally, software elements that execute control procedures for generating stimulation signals at stimulating electrodes 110a and 110b and for measuring, recording, and analyzing feedback data provided from detector electrodes 115a and 115b. In embodiments, the monitoring device may be the Stimpod™ NMS450X marketed by Xavant Technology™. In embodiments, the connector 125 may be a clip, or the like, and may include conductive contacts suitable for electrical connection to the interface 205 of assembly 100 shown in FIG. 2A. In embodiments, separate contacts may be provided for separate channels which are associated with certain electrodes or electrode pairs. In embodiments, the monitoring device 130 may be configured to mechanically connect to the interface 205 via the connector element 125 and maintain a secure connection. In embodiments, the monitoring device 130' is connected directly to the interface 205' of the diagnostic assembly 100' as described above.

Figure 2A:
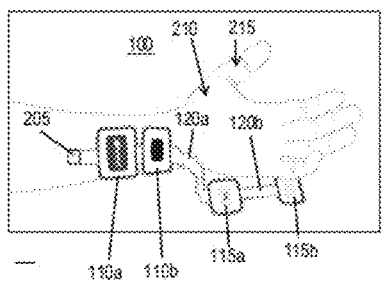
FIGS. 2A-2C illustrate different stages of attachment of the diagnostic assembly of FIG. 1 to a patient according to an exemplary embodiment of the present disclosure.
Figure 2B:
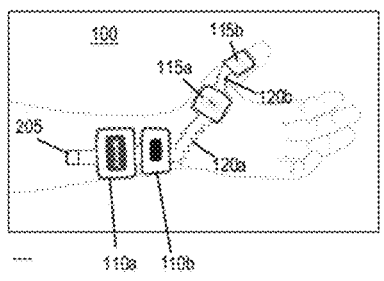
Figure 2C:
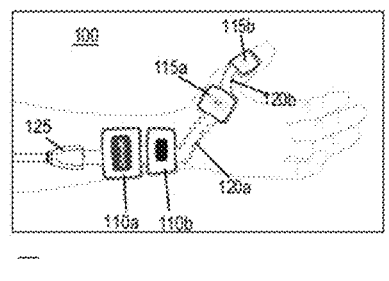

FIGS. 2A, 2B, and 2C respectively illustrate three (3) different stages of attaching the diagnostic assembly 100 of FIG. 1 to a patient's wrist and hand according to an exemplary embodiment of the present disclosure. As noted above, the assembly 100 may be attached to other parts of the patient's body, such as the patient's foot for example.

As shown in FIG. 2A, electrodes 110a and 110b, which may be mounted on or embodied in adhesive patches 111a, 111b or segments may be adhered to patient's skin at locations corresponding to the ulnar nerve, along a course of the ulnar nerve in the patient's arm. In FIG. 2B, the electrode 115a may be adhered to the patient's skin at a location corresponding to the adductor pollicis muscle and the electrode 115b may be adhered to the patient's skin at location on the user's thumb. As noted above, in embodiments, the detector electrodes 115a, 115b may be positioned elsewhere and are used to detect muscle movement in response to stimulation provided by the stimulating electrodes 110a, 110b. In FIG. 2C, the connector 125 is connected to interface 205 of assembly 100.

Figure 2D:
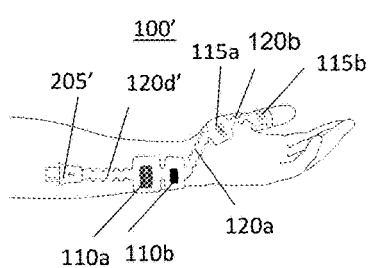
FIG. 2D illustrates the diagnostic assembly of FIG. 1A disconnected from the monitoring device in accordance with an embodiment of the present disclosure.
Figure 2E:
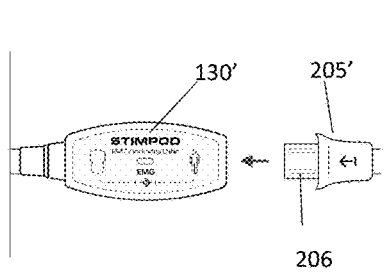
FIG. 2E illustrates a more detailed view of a connection between the diagnostic assembly of FIG. 1A and the monitoring device in accordance with an embodiment of the present disclosure.
Figure 2F:
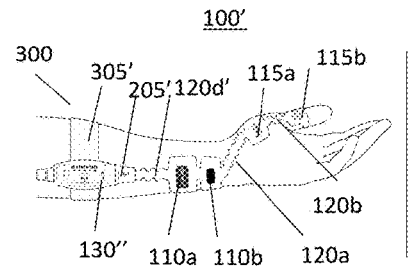
FIG. 2F illustrates the diagnostic assembly of FIG. 1A connected to a monitoring device which is secured to a user's arm using a connector interface including a strap in accordance with an embodiment of the present disclosure.

FIG. 2D illustrates the diagnostic assembly 100' connected to the user's hand 105 and directly connected to the monitoring device 130'. FIG. 2D illustrates a more detailed view of the slot 131 included in the monitoring device 130' that receives the electrode plate 206 that extends from the interface 205' to provide a physical and electrical connection. FIG. 2F illustrates the monitoring device 130' being secured to the user's arm using a connector interface 300' with a strap 305' that may wrap around the patient's arm.

Figure 9:
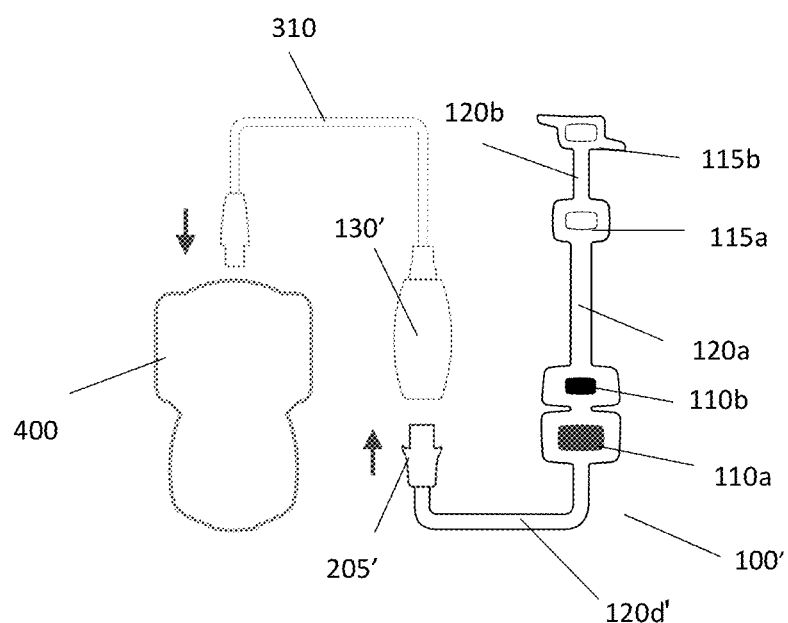
FIG. 9 illustrates an exemplary schematic showing connection between the diagnostic assembly of FIG. 1A, the monitoring device and a computer system 400 in accordance with an embodiment of the present disclosure.

As described above and shown in FIG. 1, connector 125 may be connected to monitoring device 130. In embodiments, the monitoring device 130, 130' may be in communication with one or more additional computing devices 400 (see FIG. 9, for example) for programming stimulating signals to be generated at electrodes 110a and 110b and for recording and analyzing the feedback data detected at electrodes 115a and 115b. In embodiments, the monitoring device 130, 130' may include at least one processor and at least one memory. In embodiments, the memory may include processor executable code that when executed by the processor generates stimulation signals to be provided to the electrodes 110a, 110b and receives feedback data from at least one of the electrodes 115a, 115b related to a response of the patient to the stimulation signals. In embodiments, the memory may include instructions that when processed by the processor store the feedback data in the memory. In embodiments, the memory may include instructions that when executed by the processor transmit the feedback data to another computer system via a wired or wireless connection or communication network. In embodiments, the monitor device may include one or more display elements. In embodiments, the memory may include instructions that when executed by the processor generate a graphical user interface that is displayed on the display element and may indicate the feedback data received or a representation thereof. In embodiment, the memory may include instructions to process the feedback data in order to provide the representation of the feedback data on the display.

Figure 3:
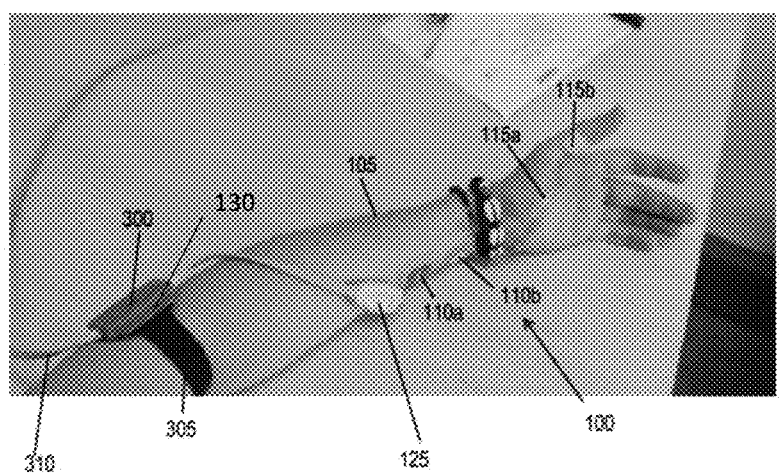
FIG. 3 illustrates another view of the exemplary connector interface for use with the diagnostic assembly of FIG. 1 according to an exemplary embodiment of the present disclosure.
Figure 3B:
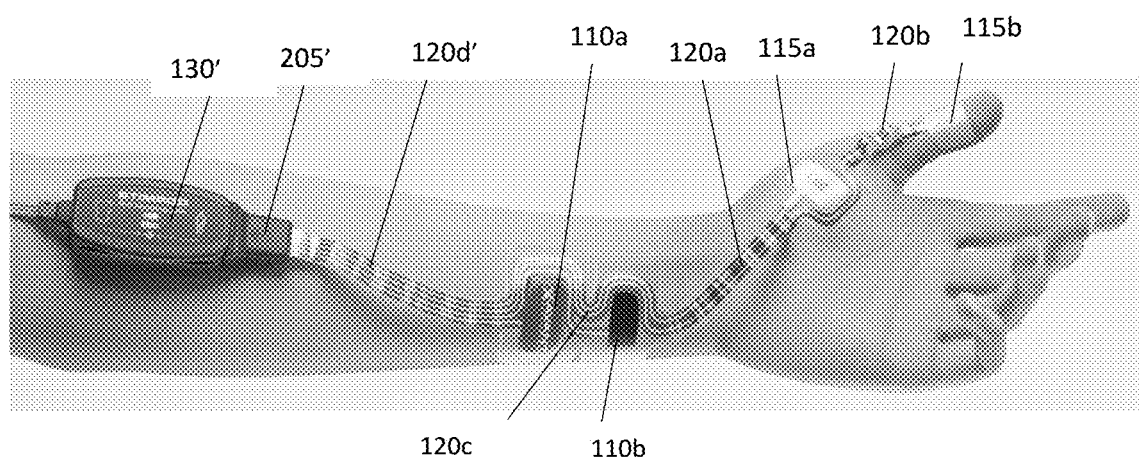
FIG. 3B illustrates another view of the diagnostic assembly of FIG. 1A connected to the monitoring device.
Figure 4A:
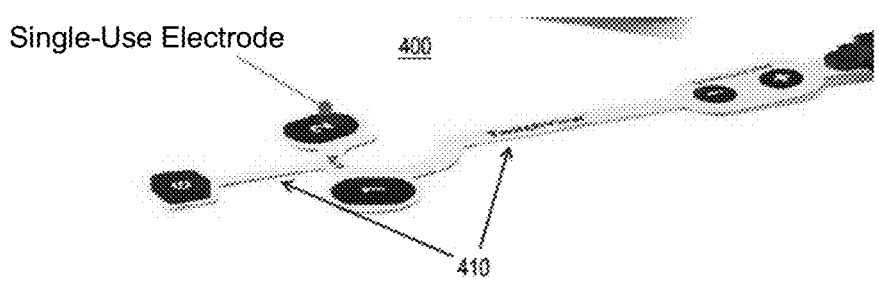
FIGS. 4A and 4B are diagrams illustrating conventional diagnostic assemblies.
Figure 4B:
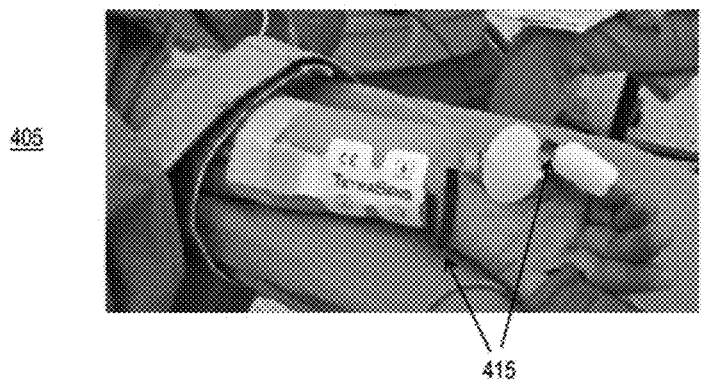

Additionally, in embodiments, one or more straps 305 may be provided to connect connector 125 and monitoring device 130 to a patient's arm to further reduce the strain on the adhesion of assembly 100 to the patient's skin. FIGS. 1 and 3 illustrate a connector interface 300 incorporating a strap 305 for strapping the wired connection between connector 125 and monitoring device 130 to the patient's arm 105. As shown in FIGS. 1 and 3, connector 125 connected to assembly 100 is, in turn, connected to connector interface 300, which incorporates strap 305. In embodiments, strap 305 may be an elastic strap with an adjustable fastener, such as hook and loop and the like, for a fitted attachment to the patient's arm—e.g., elbow. As further shown in FIG. 3, a wire 310 may be connected to connector interface 300 for providing connection to an external computer system (e.g. computer system 400 of FIG. 9). Advantageously, connector interface 300 and strap 305 further provides for securing assembly 100 to the patient's skin by reducing strain on the adhesion of assembly 100 potentially caused by the weight and/or entanglement of the wired connection to monitoring device 130. A connector interface 300' including the strap 305' may be used to secure the monitor device 130' to the user's arm in a similar manner.

While particular embodiments of the present disclosure have been shown and described in detail, it would be obvious to those skilled in the art that various modifications and improvements thereon may be made without departing from the spirit and scope of the disclosure. It is therefore intended to cover in the appended claims all such modifications and improvements that are within the scope of this disclosure.

What is claimed is:

1. A non-invasive diagnostic assembly comprising:
   an interface configured for connection to a monitoring device;
   a plurality of electrodes configured for adhesion to a patient's skin at respective locations and electrically connected to the interface; and
   at least one adjustable connection segment connecting at least two electrodes of the plurality of electrodes,
   the at least one adjustable connection segment includes:
   a plurality of segment elements connected to each other such that the at least one adjustable connection segment expands when force is applied in a first direction and contracts when force is applied in a second direction, opposite the first direction,
   each segment element of the plurality of segment elements connects to an adjacent segment element using a living hinge, such that each segment element of the plurality of segments elements is movable relative to an adjacent segment element and each segment element moves in the same direction when force is applied in the first direction and when force is applied in the second direction;

wherein the plurality of segment elements are electrically conductive and connected to each other electrically.

2. The non-invasive diagnostic assembly of claim 1, wherein the at least one adjustable connection segment comprises a conductor element providing an electrical connection between the at least two electrodes.

3. The non-invasive diagnostic assembly of claim 1, wherein the at least one adjustable connection segment comprises a conductor element providing an electrical connection between the at least two electrodes.

4. The non-invasive diagnostic assembly of claim 1, further comprising a second adjustable connection segment connecting at least one of the at least two electrodes to a third electrode.

5. The non-invasive diagnostic assembly of claim 4, wherein the second adjustable connection segment comprises a conductor element providing an electrical connection between the at least one electrode of the at least two electrodes and the third electrode.

6. The non-invasive diagnostic assembly of claim 5, wherein the second adjustable connection segment comprises a second plurality of segment elements connected to each other such that the second connection segment expands when force is applied in a first direction and contracts when force is applied in a second direction, opposite the first direction.

7. The non-invasive diagnostic assembly of claim 1, wherein the least two electrodes of the plurality of electrodes are configured for connection to the patient's skin at respective locations along an ulnar nerve.

8. The non-invasive diagnostic assembly of claim 1, wherein at least one electrode of the plurality of electrodes is configured for connection to the patient's skin at a location corresponding to an adductor pollicis muscle of the patient.

9. The non-invasive diagnostic assembly of claim 1, wherein at least one electrode of the plurality of electrodes is configured for connection to the patient's skin at a location corresponding to a flexor hallucis brevis muscle of the patient.

10. The non-invasive diagnostic assembly of claim 1, wherein at least one electrode of the plurality of electrodes is configured for connection to the patient's skin at a location corresponding to a digit on the patient's hand.

11. The non-invasive diagnostic assembly of claim 1, wherein at least one electrode of the plurality of electrodes is configured for connection to the patient's skin at a location corresponding to a thumb of the patient.

12. The non-invasive diagnostic assembly of claim 1, wherein at least one electrode of the plurality of electrodes is configured for connection to the patient's skin at a location corresponding to a pinky of the patient.

13. The non-invasive diagnostic assembly of claim 1, wherein the at least two electrodes include a first electrode adhered at a location corresponding to the adductor pollicis muscle and a second electrode adhered at a location corresponding to the thumb.

14. The non-invasive diagnostic assembly of claim 1, wherein the at least two electrodes include a first electrode adhered at a location corresponding to the adductor digiti minimi muscle and a second electrode adhered at a location corresponding to the pinky.

15. The non-invasive diagnostic assembly of claim 1, wherein the at least two electrodes include a first electrode adhered at a location corresponding to the adductor digiti minimi muscle and a second electrode adhered at a respective location corresponding to the ulnar nerve.

16. The non-invasive diagnostic assembly of claim 1, wherein the at least two electrodes include a first electrode adhered at a location corresponding to the adductor pollicis muscle and a second electrode adhered at a location corresponding to the ulnar nerve.

17. The non-invasive diagnostic assembly of claim 1, wherein the interface is directly connected to a monitoring device.

18. The non-invasive diagnostic assembly of claim 1, wherein the interface is configured for electrical connection to a monitoring device to provide data from the plurality of electrodes to the monitoring device.

19. The non-invasive diagnostic assembly of claim 1, wherein the plurality of electrodes includes at least two stimulating electrodes and at least two detector electrodes.

* * * * *